United States Patent
Inui et al.

(10) Patent No.: US 12,428,467 B2
(45) Date of Patent: Sep. 30, 2025

(54) GELATIN PARTICLES, METHOD FOR PRODUCING GELATIN PARTICLES, GELATIN PARTICLE-CONTAINING CELL, AND METHOD FOR PRODUCING GELATIN PARTICLE-CONTAINING CELL

(71) Applicants: Konica Minolta, Inc., Tokyo (JP); Yasuhiko Tabata, Tokyo (JP)

(72) Inventors: Chie Inui, Hino (JP); Akihiro Maezawa, Hino (JP); Yasuhiko Tabata, Uji (JP)

(73) Assignees: Yasuhiko Tabata, Tokyo (JP); KONICA MINOLTA, INC., Tokyo (JP)

( * ) Notice: Subject to any disclaimer, the term of this patent is extended or adjusted under 35 U.S.C. 154(b) by 56 days.

(21) Appl. No.: 18/304,159

(22) Filed: Apr. 20, 2023

(65) Prior Publication Data
US 2023/0250153 A1 Aug. 10, 2023

Related U.S. Application Data

(62) Division of application No. 16/064,828, filed as application No. PCT/JP2016/087805 on Dec. 19, 2016, now abandoned.

(30) Foreign Application Priority Data

Dec. 25, 2015 (JP) ................ 2015-254950

(51) Int. Cl.
| | | |
|---|---|---|
| C07K 14/78 | (2006.01) | |
| A61K 9/14 | (2006.01) | |
| A61K 47/42 | (2017.01) | |
| A61K 49/00 | (2006.01) | |
| C08J 3/12 | (2006.01) | |
| C08J 3/24 | (2006.01) | |

(52) U.S. Cl.
CPC ............... *C07K 14/78* (2013.01); *A61K 9/14* (2013.01); *A61K 47/42* (2013.01); *A61K 49/00* (2013.01); *C08J 3/12* (2013.01); *C08J 3/24* (2013.01); *C08J 2393/00* (2013.01)

(58) Field of Classification Search
CPC ............... C07K 14/78; C08J 3/24; A61K 9/14
See application file for complete search history.

(56) References Cited

U.S. PATENT DOCUMENTS

| | | |
|---|---|---|
| 2006/0034925 A1 | 2/2006 | Au et al. |
| 2008/0003292 A1 | 1/2008 | Ahlers et al. |
| 2009/0004278 A1 | 1/2009 | Aimi et al. |
| 2014/0179803 A1 | 6/2014 | Van Den Broek et al. |
| 2014/0193508 A1 | 7/2014 | Bajpayee et al. |

FOREIGN PATENT DOCUMENTS

| | | | | |
|---|---|---|---|---|
| ES | E 98950826 | * | 9/1998 | ............... A61K 9/00 |
| JP | 2008-150596 | * | 7/2008 | ............... C08J 3/14 |
| JP | 2008-150596 A | | 7/2008 | |
| JP | 2009-519894 A | | 5/2009 | |
| JP | 2014-058465 A | | 4/2014 | |
| WO | WO-2008062908 A1 | * | 5/2008 | ............ A61K 31/711 |
| WO | WO 2010089873 | * | 8/2010 | ............... C08J 3/12 |
| WO | WO-2010089873 A1 | * | 8/2010 | ............... C08J 3/12 |
| WO | 2014/192909 A1 | | 12/2014 | |

OTHER PUBLICATIONS

Patra et al., online publication of Oct. 8, 2015, Synthesis of gelatin nano/submicron particles by binary nonsolvent aided coacervation (BNAC) method, Materials Science and Engineering, 59: 310-318.*
Bajpai et al., 2006, Design of gelatin nanoparticles as swelling controlled delivery system for chloroquine phosphate, J Mater Sci: Mater Med, 17: 345-358.*
Goswami et al., 2010, Designing Gelatin Nanocarriers as a Swellable System for Controlled Release of insulin: An In-Vitro Kinetic Study, Journal of Macromolecular Science, Part A, Pure and Applied Chemistry, 47: 119-130.*
Terao et al., 2004, Gelatin Microspheres Crosslinked with gamma-ray: Preparation, Sorption of Proteins, and Biodegradability, Journal of Applied Polymer Science, 91: 3083-3087.*
Reddy et al., 2015, Crosslinking biopolymers for biomedical applications, Trends in Biotechnology, 33(6): 362-369.*
Foox et al., 2015, Drug Delivery from gelatin-based systems, Expert opinion on Drug Delivery, 12(9): 1547-1563.*
Esposito et al., 1996, Gelatin microspheres: influence of preparation parameters and thermal treatment on chemico-physical and biopharmaceutical properties, Biomaterials, 17: 2009-2020.*
Chou et al., 2014, The Effect of Microwave Treatment on the Drug Release Property of Gelatin Microspheres, The 15th International Conference on Biomedical Engineering, IFMBE Proceedings, J. Goh (ed.), 43: 726-729.*
Bruschi et al., 2003, Gelatin microparticles containing propolis obtained by spray-drying technique: preparation and characterization, International Journal of Pharmaceutics, 264: 45-55.*
International Search Report dated Mar. 21, 2017 from corresponding International Application No. PCT/JP2016/087805 and English translation.
Written Opinion of the International Searching Authority dated Mar. 21, 2017 from corresponding International Application No. PCT/JP2016/087805 and English translation.
Preparation of biodegradable gelatin nanospheres with a narrow size distribution for carrier of cellular internalization of plasmid DNA by Norin Doi, Jun-Ichiro Jo and Yasuhiko Tabafa; Journal of Biomaterials Science 23 (2012) pp. 991-1004.

(Continued)

*Primary Examiner* — Amber D Steele
(74) *Attorney, Agent, or Firm* — LUCAS & MERCANTI, LLP

(57) ABSTRACT

Disclosed herein are gelatin particles including gelatin, wherein when a major-axis length of dried gelatin particles is defined as a and a major-axis length of gelatin particles after swelling treatment obtained by immersing the dried gelatin particles in water at 40° C. under an atmospheric pressure for 60 minutes is defined as b, swelling degree represented by b/a is 1.0 or more but 10.0 or less, and wherein the gelatin particles after swelling treatment have a particle diameter of 1.0 nm or more but 5.0 μm or less. The gelatin particles are easily taken up by cells themselves.

11 Claims, No Drawings

(56) References Cited

OTHER PUBLICATIONS

Kaul et al,; 2022, Long-Circulating poly(ethylene glycol)-modified gelatin nanoparticles for intracellular delivery, Pharmaceutical Research, 19(7): 1061-1067.
JPO, Office Action for the corresponding Japanese patent application No. 2017-558121, dated May 12, 2020, with English translation (9 pages).
Goswami et al.; 2010, Designing gelatin nanocarriers as a swellable system for controlled release of insulin: An in-vitro kinetic study; Journal of Macromolecular Science, 47: 119-130.
Gu et al.; 2009, Novel glycidyl methacrylated dextran/gelatin nanoparticles loaded with basic fibroblast growth factor: formulation and characteristics, Drug Development and Industrial Pharmacy, 35(12): 1419-1429.
Jatariu (Cadinoiu) et al.; 2012, Double crosslinked interpenetrated network in nanoparticle form for drug targeting—Preparation, characterization and biodistribution studies, International Journal of pharmaceutics, 436: 66-74.
Sun et al.; 2009, Studies on the particle size control of gelatin microspheres, Front. Chem. China, 4(2): 222-228.
Nguyen et al.; Feb. 2015, Gelatin methacrylate microspheres for growth factor controlled release, Acta Biomater, 13: 101-110.
Elzoghby et al.; 2013, Gelatin-based nanoparticles as drug and gene delivery systems: Reviewing three decades of research, Journal of Controlled Release, 172: 1075-1091.

\* cited by examiner

GELATIN PARTICLES, METHOD FOR PRODUCING GELATIN PARTICLES, GELATIN PARTICLE-CONTAINING CELL, AND METHOD FOR PRODUCING GELATIN PARTICLE-CONTAINING CELL

CROSS REFERENCE TO RELATED APPLICATIONS

This application is a divisional of U.S. application Ser. No. 16/064,828 filed Jun. 21, 2018, which is a 371 of PCT/JP2016/087805 filed on Dec. 19, 2016, which, in turn, claimed the priority of Japanese Patent Application No. 2015-254950 filed on Dec. 25, 2015, and all applications are incorporated herein by reference.

TECHNICAL FIELD

The present invention relates to gelatin particles, a method for producing gelatin particles, a gelatin particle-containing cell, and a method for producing a gelatin particle-containing cell.

BACKGROUND ART

Gelatin is highly biocompatible and has the property of being degraded and readily absorbed by the body. Therefore, a technique has been developed in which a substance such as a reagent or a drug (hereinafter, simply referred to as "reagent or the like") encapsulated in gelatin in the form of particles is delivered and released in the living body.

For example, Patent Literature 1 discloses solid spherical swellable gelatin particles made of thermally-crosslinked gelatin having a jelly strength of 80 to 120 g. The dried gelatin particles before swelling have a particle diameter of 20 to 1600 μm, and the dried gelatin particles after swelling have a particle diameter of 50 to 2000 μm. According to Patent Literature 1, the swellable gelatin particles have excellent shape retentivity and are hard to break even when deformed by the application of external stress, and are therefore suitable for intravascular administration using a microcatheter or a syringe needle.

CITATION LIST

Patent Literature

Patent Literature 1: JP 2014-58465 A

SUMMARY OF INVENTION

Technical Problem

The gelatin particles disclosed in Patent Literature 1 are considered to be suitable for use in so-called drug delivery system (DDS) in which the gelatin particles are administered into a blood vessel, an organ, or the like to delivery and release a reagent or the like.

Meanwhile, in recent years, there is an increasing demand for the technique of directly introducing a reagent or the like into living cells. For example, when a contrast medium is introduced into living cells, the activity of the cells can be non-destructively examined. Further, when living cells having a contrast medium introduced thereinto are transplanted into a patient, it is possible to externally and less-invasively examine whether or not the transplanted cells have been colonized without incising a transplantation site again. Since gelatin has high biocompatibility, gelatin particles are considered to be suitable also as carriers to carry a reagent or the like to be introduced into living cells.

An electroporation method or a microinjection method may be used to introduce gelatin particles carrying a reagent or the like into living cells. However, such a method is performed by changing the shape of the cell membrane to introduce a reagent or the like into the inside of the cell membrane, and therefore there is a fear that the cell membrane is partially broken so that the activity of cells is reduced. From the viewpoint of minimizing such a reduction in the activity of cells, a reagent or the like is preferably taken up into cells by cell's own action. Therefore, gelatin particles carrying a reagent or the like are also preferably easily taken up into cells by cell's own action. However, according to the findings of the present inventors, the gelatin particles disclosed in Patent Literature 1 are hard to be taken up into cells by cell's own action.

In light of the above problems, it is an object of the present invention to provide gelatin particles that are easily taken up into cells by cell's own action, a method for producing such gelatin particles, a cell having such gelatin particles, and a method for producing a cell having such gelatin particles.

Solution to Problem

In order to achieve the above object, the present invention provides the following means.

[1] Gelatin particles, wherein when a major-axis length of dried gelatin particles is defined as a and a major-axis length of gelatin particles after swelling treatment obtained by immersing the dried gelatin particles in water at 40° C. under an atmospheric pressure for 60 minutes is defined as b, swelling degree represented by b/a is 1.0 or more but 10.0 or less, and wherein the gelatin particles after swelling treatment have a particle diameter of 1.0 nm or more but 5.0 μm or less.

[2] The gelatin particles according to [1], wherein the dried gelatin particles have an aspect ratio of 1.0 or more but 1.4 or less.

[3] The gelatin particles according to [1] or [2], wherein the major-axis length b of the gelatin particles after swelling treatment is 2.0 μm or less.

[4] The gelatin particles according to any one of [1] to [3], further including a contrast medium.

[5] The gelatin particles according to any one of [1] to [4], wherein the gelatin has been crosslinked.

[6] A method for producing gelatin particles, including discharging droplets of a liquid containing melted gelatin into an atmosphere in a heating tube or a drying chamber whose difference in temperature from the droplets is 235° C. or less and drying the droplets to obtain gelatin particles.

[7] The method for producing gelatin particles according to [6], wherein the droplets are discharged from a nozzle of an inkjet head.

[8] A gelatin particle-containing cell, wherein the gelatin particles according to any one of [1] to [5] are contained inside a cell membrane.

[9] A method for producing a gelatin particle-containing cell, including adding the gelatin particles according to any one of [1] to [5] and a cell to a liquid to allow the gelatin particles to be taken up inside a cell membrane of the cell by action of the cell.

Advantageous Effects of Invention

According to the present invention, it is possible to provide gelatin particles that are easily taken up by cells themselves, a method for producing such gelatin particles, a cell having such gelatin particles, and a method for producing a cell having such gelatin particles.

DESCRIPTION OF EMBODIMENTS

In order to achieve the above object, the present inventors have intensively studied conditions required of gelatin particles that are easily taken up into cells by cell's own action. As a result, the present inventors have found that gelatin particles whose swelling degree when absorbing water is low and whose particle diameter after swelling in water is 1.0 nm or more but 5.0 μm or less are easily taken up into cells by cell's own action. This finding has led to the completion of the present invention.

Hereinbelow, exemplary embodiments of the present invention will be described in detail.

1. Gelatin Particles and Method for Producing the Same

This embodiment relates to gelatin particles and a method for producing gelatin particles.

1-1. Gelatin Particles

The gelatin particles according to this embodiment are gelatin particles including gelatin, wherein when a major-axis length of dried gelatin particles is defined as a and a major-axis length of gelatin particles after swelling treatment obtained by immersing the dried gelatin particles in water at 40° C. under an atmospheric pressure for 60 minutes is defined as b, swelling degree represented by b/a is 1 or more but 10 or less, and wherein the gelatin particles after swelling treatment have a particle diameter of 1.0 nm or more but 5.0 μm or less. As will be described later, gelatin particles having such a structure as described above are easily taken up by cells, and are therefore also referred to as "easy-uptake gelatin particles" in this description. The easy-uptake gelatin particles may be single particles or aggregates of two or more gelatin particles.

It is to be noted that in this description, the dried gelatin particles refer to gelatin particles dried by allowing them to stand in the atmosphere at 80° C. for 24 hours. Further, in this description, the gelatin particles after swelling treatment refer to gelatin particles obtained by immersing dried gelatin particles in water at 40° C. under the atmospheric pressure for 60 minutes.

The minor-axis length and major-axis length of the easy-uptake gelatin particles may be values obtained by analyzing an image taken by a scanning electron microscope (SEM). When the gelatin particles are the above-described aggregates, the major-axis length, minor-axis length, particle diameter, and aspect ratio of the gelatin particles may be the averages of the major-axis lengths, minor-axis lengths, particle diameters, and aspect ratios of a plurality of gelatin particles after swelling treatment (e.g., 20 gelatin particles) randomly selected from the aggregates, respectively.

The easy-uptake gelatin particles have a swelling degree of 1.0 or more but 10.0 or less. If the swelling degree is larger than 10.0, the gelatin particles absorb a larger amount of water when swelling, and are therefore likely to aggregate due to the action of absorbed water. It is considered that when many swelled gelatin particles aggregate, the apparent particle diameter of the gelatin particles increases, and therefore the gelatin particles are likely to be recognized as foreign matter by cells and are hard to be taken up into cells by cell's own action. On the other hand, the gelatin particles having a swelling degree of 10.0 or less do not absorb so much water (i.e., have a low swelling degree), and are therefore hard to aggregate even after swelling, and the apparent particle diameter of the gelatin particles is less likely to increase. Therefore, it is considered that the gelatin particles having a swelling degree of 10.0 or less are less likely to be recognized as foreign matter by cells even after swelling by absorption of water, and are therefore easily taken up into cells by cell's own action. From the above viewpoint, the swelling degree is preferably 1.0 or more but 8.0 or less, more preferably 1.0 or more but 5.0 or less.

The gelatin particles after swelling treatment have a particle diameter of 1.0 nm or more but 5.0 μm or less. The gelatin particles having a particle diameter of 5.0 μm or less are easily taken up into cells by cell's own action. The reason for this is considered to be that the gelatin particles having a particle diameter of 5.0 μm or less are less likely to be recognized as foreign matter by cells, and are therefore easily taken up into cells by action such as endocytosis. From the above viewpoint, the particle diameter of the gelatin particles after swelling treatment is preferably 2.0 μm or less, more preferably 1.5 μm or less. On the other hand, the gelatin particles having a particle diameter of 1.0 nm or more can easily carry a reagent or the like therein. From the above viewpoint, the particle diameter of the gelatin particles after swelling treatment is preferably 2.0 nm or more. Further, when having a particle diameter of 0.50 μm or more, the gelatin particles after swelling treatment are excellent in handleability and can contain a large amount of reagent or the like. It is to be noted that the particle diameter of the easy-uptake gelatin particles may be the average of the major-axis length and the minor-axis length of the gelatin particles.

The dried gelatin particles preferably have an aspect ratio of 1.0 or more but 1.4 or less. When the aspect ratio is 1.4 or less, the gelatin particles are more likely to keep their nearly-spherical shape both before and after swelling. Therefore, in a solution containing the gelatin particles and cells, the gelatin particles are likely to come into contact with the cells at contact surfaces having more uniform shape and size. From this, it is considered that there is little difference in ease of uptake among the gelatin particles. Therefore, it is considered that when the easy-uptake gelatin particles have an aspect ratio within the above range, the amount of the gelatin particles to be taken up into cells and the amount of cells that take up the gelatin particles can be more easily controlled. The aspect ratio of the easy-uptake gelatin particles may be a value determined by dividing the major-axis length of the gelatin particles by the minor-axis length of the gelatin particles.

The major-axis length (b) of the gelatin particles after swelling treatment is preferably 2.0 μm or less. It is considered that when the major-axis length (b) is 2.0 μm or less, the gelatin particles are more likely to keep their small particle diameter both before and after swelling, and are therefore easily taken into cells by cell's own action. From the above viewpoint, the major-axis length (b) is more preferably 1.8 μm or less, even more preferably 1.5 μm or less.

The easy-uptake gelatin particles are mainly made of gelatin. More specifically, the easy-uptake gelatin particles contain 300 or more glycine residues out of 1000 amino acid residues and contain both alanine and proline when analyzed with an amino acid analyzer. The gelatin is not particularly limited as long as it is capable of forming particles, and any known gelatin may be used which is obtained by denaturing collagen derived from cattle bone, cattle skin, pig skin, pig tendon, fish scales, and fish meat. Gelatin has previously been used for food and for medical purposes, and its intake into the body is hardly harmful to the human body. Further, gelatin disperses and disappears in the living body, and is therefore advantageous in that its removal from the living body is not required. It is to be noted that the easy-uptake gelatin particles may contain a component other than gelatin as long as the gelatin particles can be taken up into cells. It is to be noted that when the easy-uptake gelatin particles contain a component other than gelatin, the component is preferably contained to the extent that harm to the human body caused by intake into the body is negligible. Further, the component other than gelatin is preferably composed of a substance that does not accumulate in the living body and is easily discharged.

From the viewpoint of easily forming gelatin particles that satisfy the above-described conditions of particle diameter and swelling degree, the weight-average molecular weight of the gelatin constituting the easy-uptake gelatin particles is preferably 1000 or more but 100000 or less. The weight-average molecular weight may be a value measured in accordance with, for example, the PAGI Method Ver. 10 (2006).

The gelatin constituting the easy-uptake gelatin particles may be crosslinked. The crosslinking may be crosslinking achieved by using a crosslinking agent or self-crosslinking achieved without using a crosslinking agent.

The crosslinking agent may be, for example, a compound having a plurality of functional groups that form chemical bonds with a hydroxyl group, a carboxyl group, an amino group, a thiol group, an imidazole group, or the like. Examples of such a crosslinking agent include glutaraldehyde, water-soluble carbodiimides such as 1-ethyl-3-(3-dimethylaminopropyl)carbodiimide hydrochloride (EDC) and 1-cyclohexyl-3-(2-morpholinoethyl)carbodiimide-metho-p-toluenesulfonate (CMC), compounds having two or more epoxy groups such as ethylene glycol diglycidyl ether, polyethylene glycol diglycidyl ether, polyglycerol polyglycidyl ether, and glycerol polyglycidyl ether, and propylene oxide. Among them, from the viewpoint of further enhancing reactivity, glutaraldehyde and EDC are preferred, and glutaraldehyde is more preferred.

Examples of the self-crosslinking include crosslinking achieved by application of heat and crosslinking achieved by irradiation with electron beams or ultraviolet rays.

The easy-uptake gelatin particles may carry a reagent or the like. The phrase "gelatin particles carry a reagent or the like" means that a reagent or the like is present on the surfaces of the gelatin particles or inside the gelatin particles. From the viewpoint of retaining the reagent or the like in cells for a longer period of time, the reagent or the like is preferably present inside the gelatin particles.

Examples of the reagent or the like include: reagents to be used for tests of biological activity, measurements of substances in the living body, and quantitative analysis of substances in the living body; and drugs. Examples of the reagents include contrast media.

Examples of the contrast media include magnetic substances for use as contrast media for MRI. Examples of the contrast media for MRI include contrast media containing gadolinium (Gd) and contrast media containing iron (e.g., $Fe_3O_4$ and $\gamma$-$Fe_2O_3$).

The drugs are not particularly limited as long as they can be carried by the gelatin particles. Examples of such drugs include proteins having pharmaceutical activity, plasmids, aptamers, antisense nucleic acids, ribozymes, nucleic acids used for pharmaceutical purposes, including tRNA, snRNA, siRNA, shRNA, ncRNA, and condensed DNA, and antigens used for pharmaceutical purposes.

Examples of the proteins having pharmaceutical activity include steroids, nonsteroidal anti-inflammatory drugs (NSAIDs), vitamin A (retinoid), vitamin D3 and vitamin D3 analogs, antibiotics, antiviral drugs, and antibacterial drugs.

1-2. Method for Producing Gelatin Particles

The easy-uptake gelatin particles can be produced by a known method in which gelatin is formed into particles. Examples of such a method include: a method in which droplets of a liquid containing melted gelatin (hereinafter, also simply referred to as "gelatin solution") are discharged into an atmosphere in a heating tube or a drying chamber and dried (in-air dropping method); a method in which droplets of a gelatin solution are discharged into a hydrophobic solvent and dispersed (in-liquid dropping method); and a method in which a gelatin solution is emulsified to disperse microdroplets containing gelatin (in-liquid dispersion method). Examples of the in-air dropping method include an inkjet method and a spray drying method. Examples of the in-liquid dispersion method include an emulsion method and a coacervation method. From the viewpoint of producing gelatin particles having a more uniform particle diameter and a smaller aspect ratio, an in-air dropping method is preferred, and an inkjet method is more preferred.

According to new findings by the present inventors, an in-air dropping method is particularly preferred in which the above-described droplets are dried under conditions where a temperature change is small. It is considered that this makes it possible to prevent gelatin particles from being deformed or disintegrated due to temperature change so that gelatin particles having a particle diameter of 1.0 nm or more but 5.0 μm or less are more likely to be produced and the produced gelatin particles can have a more uniform particle diameter.

For example, in the case of an inkjet method, droplets of a gelatin solution can be discharged from an inkjet nozzle provided inside a heated heating tube and collected by a filter provided inside the same heating tube. From the viewpoint of further reducing deformation or disintegration of gelatin particles, the heating of the heating tube is preferably performed by allowing hot air to flow through the inside of the heating tube in the same direction as a direction in which the droplets are dropped (i.e., in a vertical direction from the top toward the bottom of the heating tube).

Alternatively, a spray drying method may be used. In this case, a gelatin solution is sprayed from an atomizer or a nozzle into a heated drying chamber.

From the viewpoint of further enhancing the above-described effects, the difference between the temperature of an atmosphere in the heating tube or the drying chamber and the temperature of a dropped gelatin solution is preferably 235° C. or less. Further, from the viewpoint of efficiently and stably obtaining gelatin particles, the temperature difference is preferably 20° C. or more but 200° C. or less, more preferably 20° C. or more but 100° C. or less. Particularly, the temperature of an atmosphere in the heating tube or the drying chamber is preferably higher than the temperature of droplets by 20° C. or more but 80° C. or less. The temperature of droplets is preferably 15° C. or higher but 80° C. or lower, more preferably 20° C. or higher but 50° C. or lower. The temperature of an atmosphere in the heating tube or the drying chamber is preferably 40° C. or higher but 250° C. or lower, more preferably 40° C. or higher but 150° C. or lower.

From the viewpoint of making gelatin particles whose particle diameter after swelling treatment is 1.0 nm or more but 5.0 μm or less more likely to be produced, the gelatin content of the gelatin solution is preferably $1.00 \times 10$ vol % or more but 60 vol % or less, more preferably $1.00 \times 10^{-7}$ vol % or more but 50 vol % or less, even more preferably $1.00 \times 10^{-7}$ vol % or more but 20 vol % or less.

From the viewpoint of making gelatin particles having a swelling degree of 1.0 or more but 10.0 or less more likely to be produced, gelatin particles are preferably crosslinked.

The crosslinking of gelatin particles may be crosslinking achieved using the above-mentioned crosslinking agent or self-crosslinking achieved by application of heat or by irradiation with electron beams or ultraviolet rays.

When easy-uptake gelatin particles carrying a reagent or the like are produced, a gelatin solution obtained by previously mixing gelatin and a reagent or the like may be used to form the gelatin into particles.

2. Cell

This embodiment relates to a cell containing easy-uptake gelatin particles inside the cell membrane and a method for producing such a cell.

2-1. Cell

The cell according to this embodiment is a cell containing easy-uptake gelatin particles inside the cell membrane (hereinafter, also referred to as "gelatin particle-containing cell").

The phrase "containing gelatin particles inside the cell membrane" means that in an image of a cell taken by a transmission electron microscope (TEM), gelatin particles are observed inside the cell membrane. The uptake of gelatin particles into cells can be confirmed in the following manner. For example, when gelatin particles contain a contrast medium, the determination as to whether or not the gelatin particles containing a contrast medium have been taken up into cells can be made by staining and microscopically observing the contrast medium. When not containing a contrast medium, gelatin particles may be previously fluorescently labeled. In this case, the determination as to whether or not the fluorescently labeled-gelatin particles have been taken up into cells can be made using a confocal microscope. The fluorescent labeling of gelatin particles can be performed using, as a substrate, FITC-gelatin prepared by, for example, mixing equal amounts of a solution labeled with fluorescein isothiocyanate (FITC) (e.g., a 10 mM acetic acid solution of FITC-collagen manufactured by Cosmo Bio Co., Ltd.), 0.4 M sodium chloride, 0.04% (W/V) sodium azide, and a 50 mM tris-HCl buffer containing 10 mM calcium chloride (pH 7.5) and then heating the mixture at 60° C. for 30 minutes.

The easy-uptake gelatin particles contained in cells preferably carry a contrast medium, especially a contrast medium for MRI. Such cells are produced by a method described later in which easy-uptake gelatin particles are taken up into cells by cell's own action. Therefore, the activity of the cells can be non-destructively examined by observing the presence or absence of the contrast medium in the cells.

Examples of cells capable of containing gelatin particles inside the cell membrane include known cells including cells derived from biological samples or specimens extracted from various organs such as bone marrow, heart, lung, liver, kidney, pancreas, spleen, intestinal tract, small intestine, cardiac valve, skin, blood vessel, cornea, eyeball, dura mater, bone, trachea, and auditory ossicles, commercially-available established cell lines, stem cells such as skin stem cells, epidermal keratinocyte stem cells, retinal stem cells, retinal epithelial stem cells, cartilage stem cells, hair follicle stem cells, muscle stem cells, osteoprogenitor stem cells, preadipocyte stem cells, hematopoietic stem cells, nerve stem cells, hepatic stem cells, pancreatic stem cells, ectodermal stem cells, mesodermal stem cells, endodermal stem cells, mesenchymal stem cells, ES cells, and iPS cells, and cells differentiated from these stem cells.

Among these cells, when cells, especially stem cells and cells differentiated from stem cells, to be transplanted into a patient in cellular regenerative medicine contain easy-uptake gelatin particles carrying a contrast medium, especially a contrast medium for MRI, the determination as to whether or not the gelatin particle-containing cells have been colonized in a transplantation site can be made without reoperation by observing the contrast medium in the transplantation site after transplantation into a patient. Therefore, it is considered that these cells containing gelatin particles carrying a contrast medium for MRI can reduce the physical, mental, financial, and temporal burden on patients who receive regenerative medicine treatment and improve the quality of life (QOL) of the patients.

2-2. Method for Producing Cell

The gelatin particle-containing cell can be produced by introducing easy-uptake gelatin particles into the cell mentioned above. Examples of a method for introducing gelatin particles into a cell include a method in which gelatin particles and a cell are added to a liquid to allow the gelatin particles to be taken up into the cell by cell's own action such as endocytosis and a method in which gelatin particles are introduced into a cell by external operation. Examples of the method in which gelatin particles are taken up into a cell by cell's own action include a method in which gelatin particles and cells are stirred in a liquid and a method in which cells are cultured in a cell culture medium containing gelatin particles. It is to be noted that the above-described easy-uptake gelatin particles are very efficiently taken up by cells themselves, and therefore it is not particularly necessary to perform operation for forming a complex with another component to promote uptake into cells. From the viewpoint of minimizing a reduction in the activity of cells, among the above methods, a method is preferred in which cells are mixed with easy-uptake gelatin particles in a liquid and cultured. Examples of the method in which gelatin particles are introduced into a cell by external operation include an electroporation method and a microinjection method. Among them, from the viewpoint of preventing a reduction in the activity of cells during the introduction of gelatin particles, a method in which gelatin particles are introduced into a cell by cell's own action is preferred, and a method in which gelatin particles are taken up into a cell without forming the above-described complex is more preferred.

The liquid to which gelatin particles and cells are added may be a cell culture medium. The cell culture medium may be a known buffer or physiological saline, and examples thereof include Hanks' Balanced Salt Solution (HBSS), 4-(2-hydroxyethyl)-1-piperazineethanesulfonic acid (HEPES), and another known phosphate buffered saline (PBS).

From the viewpoint of enhancing the activity of cells to facilitate the uptake of gelatin particles into the cells by cell's own action, the temperature of the cell culture medium during stirring is preferably 15° C. or higher but 50° C. or lower, more preferably 35° C. or higher but 45° C. or lower.

When gelatin particles are introduced into the inside of the cell membrane by cell's own action, introduction of gelatin particles may be promoted by, for example, shaking the cell culture medium containing the gelatin particles and the cells.

It is considered that when gelatin particles are introduced into cells by cell's own action, high-activity cells are more likely to take up gelatin particles, but low-activity cells are less likely to take up gelatin particles. Therefore, the activity of cells can be non-destructively examined by adding gelatin particles carrying a contrast medium and cells to a liquid and, if necessary, shaking the liquid, and then by observing the presence or absence of the contrast medium in the cells.

EXAMPLES

Hereinbelow, specific examples of the present invention will be described. It is to be noted that the scope of the present invention should not be construed as being limited to these examples.

tured by Yamato Scientific Co., Ltd.) at 160° C. for a predetermined time shown in Table 1. In this way, Gelatin Particles 1 to 16 were obtained.

Table 1 shows the volume percentages of gelatin and $Fe_2O_3$ in each of the raw material solutions used for producing Gelatin Particles 1 to 16, a particle production method, the quantity of each droplet when particles were produced by an inkjet method, the temperature in a system during particle production, a liquid feed rate, and the temperature and time of heating in a heating furnace.

TABLE 1

Production of Gelatin Particles 1 to 16

| | Raw material solution | | Particle production | | | | Heating (Crosslinking) | |
|---|---|---|---|---|---|---|---|---|
| | Gelatin (vol %) | $Fe_2O_3$ (vol %) | Method | Quantity of droplet (pL) | Temperature in system (° C.) | Liquid feed rate (ml/h) | Heating temperature (° C.) | Heating time (min) |
| Gelatin Particle 1 | $4.88 \times 10^{-7}$ | $4.88 \times 10^{-8}$ | Inkjet | 4 | 100 | 100 | 160 | 30 |
| Gelatin Particle 2 | $1.45 \times 10^{-7}$ | $1.45 \times 10^{-8}$ | Inkjet | 4 | 100 | 100 | 160 | 1 |
| Gelatin Particle 3 | $1.81 \times 10^{-5}$ | $1.81 \times 10^{-6}$ | Inkjet | 4 | 100 | 100 | 160 | 2 |
| Gelatin Particle 4 | $6.10 \times 10^{-2}$ | $6.10 \times 10^{-3}$ | Inkjet | 4 | 100 | 100 | 160 | 0.03 |
| Gelatin Particle 5 | 1.65 | 0.165 | Inkjet | 4 | 100 | 100 | 160 | 30 |
| Gelatin Particle 6 | $6.10 \times 10^{-2}$ | $6.10 \times 10^{-3}$ | Inkjet | 4 | 100 | 100 | 160 | 15 |
| Gelatin Particle 7 | $9.26 \times 10^{-3}$ | $9.26 \times 10^{-4}$ | Inkjet | 4 | 100 | 100 | 160 | 5 |
| Gelatin Particle 8 | $2.26 \times 10^{-3}$ | $2.26 \times 10^{-4}$ | Inkjet | 4 | 100 | 100 | 160 | 10 |
| Gelatin Particle 9 | $2.26 \times 10^{-3}$ | $2.26 \times 10^{-4}$ | Spray drying | — | 200 | 1000 | 160 | 15 |
| Gelatin Particle 10 | $2.26 \times 10^{-3}$ | $2.26 \times 10^{-4}$ | Spray drying | — | 200 | 1000 | 160 | 15 |
| Gelatin Particle 11 | $2.40 \times 10^{-3}$ | $2.40 \times 10^{-4}$ | Spray drying | 4 | 200 | 100 | 160 | 15 |
| Gelatin Particle 12 | $1.81 \times 10^{-2}$ | $1.81 \times 10^{-3}$ | Inkjet | 4 | 100 | 100 | 160 | 0.01 |
| Gelatin Particle 13 | 18.1 | 18.1 | Inkjet | 4 | 100 | 100 | 160 | 30 |
| Gelatin Particle 14 | $1.81 \times 10^{-5}$ | $1.81 \times 10^{-6}$ | Inkjet | 4 | 100 | 100 | 160 | 1.5 |
| Gelatin Particle 15 | 46.5 | 4.65 | Inkjet | 42 | 100 | 100 | 160 | 50 |
| Gelatin Particle 16 | 1.75 | 0.175 | Inkjet | 4 | 100 | 100 | 160 | 30 |

1. Production of Gelatin Particles
1-1. Preparation of Raw Material Solutions

Gelatin (G-2613P manufactured by Nitta Gelatin Inc.), pure water, $Fe_2O_3$ powder (3310DX ($\alpha$-$Fe_2O_3$) manufactured by COREFRONT Corporation) were mixed to prepare a raw material solution containing the gelatin and the $Fe_2O_3$ powder in a volume ratio of 10:1 (gelatin:$Fe_2O_3$ powder=10:1). The amounts of the gelatin and the $Fe_2O_3$ powder were adjusted so that the raw material solution had a gelatin concentration and a $Fe_2O_3$ concentration shown in Table 1.

1-2. Production of Gelatin Particles by Inkjet Method

An air flow of 3 L/min was blown into a heating tube heated to 100° C. in a vertical direction from the top toward the bottom of the heating tube. Droplets of 4 pL or 42 pL of the raw material solution heated to 40° C. were dropped from an inkjet head (512S manufactured by Konica Minolta Co., Ltd.) into the air flow at an ejecting frequency of 5 kHz and landed on a hydrophilically-treated polytetrafluoroethylene resin (PTFE) filter (Millipore, 0.45 mesh, manufactured by Merck (Nihon Millipore K.K.)) located 200 cm below the inkjet head. The dropping was performed for 5 hours, and then gelatin particles on the filter were collected.

1-3. Production of Gelatin Particles by Spray Drying Method

The raw material solution was sprayed from a two-fluid-type nozzle of a spray dryer (SPRAY BOY manufactured by PRECI Co., Ltd.) into a drying chamber heated to 200° C. at a rate of 1 kg/h, and gelatin particles were collected from the bottom of the drying chamber.

1-4. Crosslinking

The gelatin particles produced above were heated in a vacuum heating furnace (Vacuum Oven ADP200 manufac- 2. Measurement of Gelatin Particles
2-1. Major-Axis Length, Average Particle Diameter, and Aspect Ratio of Dried Gelatin Particles Gelatin particles of each of Gelatin Particles 1 to 16 produced above were imaged with a scanning electron microscope (SEM). The taken image was analyzed using Mac-View that is particle size distribution analysis software manufactured by Mountech Co., Ltd. to measure the minor-axis lengths and the major-axis lengths of randomly-selected 20 gelatin particles, and the averages thereof were defined as the minor-axis length and the major-axis length (a) of each of dried Gelatin Particles 1 to 16. The average of the minor-axis length and the major-axis length of each of the randomly-selected 20 dried gelatin particles was determined as the particle diameter of each of the 20 gelatin particles, and the average of the thus determined particle diameters of the 20 gelatin particles was defined as the average particle diameter of each of dried Gelatin Particles 1 to 16. Further, the major-axis length of each of the randomly-selected 20 dried gelatin particles was divided by the minor-axis length of each of the randomly-selected 20 dried gelatin particles to determine the aspect ratio of each of the 20 gelatin particles, and the average of the thus determined aspect ratios of the 20 gelatin particles was defined as the aspect ratio of each of dried Gelatin Particles 1 to 16.

2-2. Swelling Treatment and Major-Axis Length and Average Particle Diameter of Gelatin Particles after Swelling Treatment First, 0.1 g of gelatin particles of each of Gelatin Particles 1 to 16 produced above were immersed and dispersed in 100 mL of pure water at 40° C. and were allowed to stand for 60 minutes (swelling treatment). Then, the gelatin particles were imaged with a scanning electron microscope (SEM). The taken image was analyzed using Mac-View that is particle size distribution analysis software manufactured by Mountech Co., Ltd. to measure the minor-axis length and the major-axis length of each of randomly-selected 20 gelatin particles, and the average of the thus measured minor-axis length and major-axis length was determined as the particle diameter of each of the 20 gelatin particles. The average of the thus determined particle diameters of the 20 gelatin particles was defined as the average particle diameter of each of Gelatin particles 1 to 16 after swelling treatment.

2-3. Swelling Degree

The average particle diameter of gelatin particles after swelling treatment was divided by the average particle diameter of dried gelatin particles to determine the swelling degree of each of Gelatin Particles 1 to 16.

Table 2 shows the major-axis lengths, average particle diameters, and aspect ratios of dried Gelatin Particles 1 to 16 and the swelling degrees of Gelatin Particles 1 to 16.

(Composition of Fe Staining Solution)

Equal volumes of the following two solutions were mixed to prepare an Fe staining solution.
20 vol % HCL (5-fold dilution of concentrated hydrochloric acid)
10 mass % aqueous $K_4(Fe(CN_6))$ solution (100 mg/mL)

(Composition of Nuclear Staining Solution)

Five parts by mass of ammonium sulfate and 0.1 parts by mass of Nuclear fast red were mixed with 100 parts by mass of distilled water to prepare a nuclear staining solution.

(Counting of Number of Cells that have Taken Up Fe)

The stained cells were observed with an optical microscope to evaluate whether stained Fe was contained in randomly-selected 20 cells.

In the cases of the cell suspensions of Gelatin Particles 1 to 11 whose swelling degree was 1 or more but 10 or less and average particle diameter after swelling treatment was 1.0 nm or more but 5.0 µm or less, out of the 20 cells, 10% or more of the cells (2 or more cells) were confirmed to have taken up gelatin inside the cell membrane.

TABLE 2

Major-Axis Lengths, Average Particle Diameters, and Aspect Ratios of Dried Gelatin Particles 1 to 16 and Swelling Degrees of Gelatin Particles 1 to 16

| | Under dry conditions | | | | After swelling treatment | | |
|---|---|---|---|---|---|---|---|
| | Minor-axis length (µm) | Major-axis length (a) (µm) | Average particle diameter (µm) | Aspect ratio | Major-axis length (b) (µm) | Average particle diameter (µm) | Swelling degree (b/a) |
| Gelatin Particle 1 | 0.029 | 0.031 | 0.03 | 1.07 | 0.034 | 0.03 | 1.1 |
| Gelatin Particle 2 | 0.020 | 0.020 | 0.02 | 1.00 | 0.080 | 0.08 | 4.0 |
| Gelatin Particle 3 | 0.098 | 0.102 | 0.10 | 1.04 | 0.918 | 0.90 | 9.0 |
| Gelatin Particle 4 | 1.463 | 1.537 | 1.50 | 1.05 | 4.611 | 4.50 | 3.0 |
| Gelatin Particle 5 | 4.390 | 4.610 | 4.50 | 1.05 | 5.071 | 4.95 | 1.1 |
| Gelatin Particle 6 | 1.463 | 1.537 | 1.50 | 1.05 | 2.306 | 2.25 | 1.5 |
| Gelatin Particle 7 | 0.780 | 0.820 | 0.80 | 1.05 | 1.640 | 1.60 | 2.0 |
| Gelatin Particle 8 | 0.488 | 0.512 | 0.50 | 1.05 | 1.024 | 1.00 | 2.0 |
| Gelatin Particle 9 | 0.417 | 0.583 | 0.50 | 1.49 | 0.875 | 0.75 | 1.5 |
| Gelatin Particle 10 | 0.357 | 0.643 | 0.50 | 1.80 | 0.965 | 0.75 | 1.5 |
| Gelatin Particle 11 | 0.498 | 0.522 | 0.51 | 1.05 | 1.044 | 1.02 | 2.0 |
| Gelatin Particle 12 | 0.976 | 1.024 | 1.00 | 1.49 | 12.288 | 12.00 | 12.0 |
| Gelatin Particle 13 | 9.756 | 10.244 | 10.00 | 1.05 | 51.220 | 50.00 | 5.0 |
| Gelatin Particle 14 | 0.098 | 0.102 | 0.10 | 1.04 | 1.530 | 1.50 | 15.0 |
| Gelatin Particle 15 | 29.268 | 30.732 | 30.00 | 1.05 | 61.464 | 60.00 | 2.0 |
| Gelatin Particle 16 | 4.545 | 4.636 | 4.59 | 1.02 | 5.100 | 5.05 | 1.1 |

3. Introduction into Cells and Evaluations

A cell culture medium was used which was prepared by adding 50 mL of fetal bovine serum to 500 mL of a cell culture medium MEM Alpha basic (1×) manufacture by Life Technologies. One milligram of each of Gelatin Particles 1 to 16 was added to 3 mL of the cell culture medium, and mouse osteoblast-derived cells (MC3T3E1) were added at 6000 cells/mL. The cell culture medium after cell addition was incubated at 40° C. for 24 hours. In this way, 16 evaluation samples were prepared.

Then, part of each of the cell suspensions was taken out, and the determination as to whether or not gelatin taken up inside the cell membrane could be confirmed was made in the following manner.

(Staining of Cells and Fe)

First, 1 ml of 1% paraformaldehyde was added to the cultured cells to perform cell immobilization treatment. Then, 1 ml of an Fe staining solution having the following composition was added to stain Fe. Further, 1 mL of a nuclear staining solution adjusted to the following concentration was added to stain the cells.

On the other hand, in the cases of the cell suspensions of Gelatin Particles 12, 13, 15, and 16 whose average particle diameter after swelling treatment was 5.0 µm or more, out of the 20 cells, less than 10% of the cells (less than 2 cells) took up the gelatin particles inside the cell membrane. The reason for this is considered to be that cells recognized the gelatin particles as foreign matter due to their large average particle diameter after swelling treatment, and therefore the gelatin particles were hard to be taken up into cells by cell's own action.

Further, in the cases of the cell suspensions of Gelatin Particle 14 whose swelling degree was larger than 10, out of the 20 cells, less than 10% of the cells (less than 2 cells) took up the gelatin particles inside the cell membrane. The reason for this is considered to be that since the gelatin particles absorbed a large amount of water and aggregated, cells recognized the gelatin particles as foreign matter due to their large apparent particle diameter, and therefore the gelatin particles were hard to be taken up into cells by cell's own action.

It is to be noted that Gelatin Particles 1 to 8 produced by an inkjet method generally had a small aspect ratio. For example, Gelatin Particle 8 had a smaller aspect ratio than Gelatin Particles 9 and 10 having the same particle diameter as Gelatin Particle 8 and produced by a spray drying method.

This application is based upon and claims the benefit of priority from prior Japanese Patent Application No. 2015-254950 filed on Dec. 25, 2015 in Japan, the specification and claims of which are incorporated herein by reference.

INDUSTRIAL APPLICABILITY

The gelatin particles according to the present invention can contain, for example, a contrast medium for MRI and can be introduced into cells for transplantation used in regenerative medicine. Such cells are produced by allowing the gelatin particles to be taken up by cell's own action, and the activity of the cells can be non-destructively examined by observing the presence or absence of the contrast medium in the cells by MR imaging. Therefore, it is considered that the use of the gelatin particles according to the present invention makes it possible to reduce the wastage rate of cells used in regenerative medicine and increase the use efficiency of the cells. Further, when such cells are transplanted, a transplantation site can be observed not by reoperation but by MR imaging to determine whether or not the cells have been colonized in the transplantation site. Therefore, it is considered that the gelatin particles according to the present invention can reduce the physical, mental, financial, and temporal burdens on patients and improve the quality of life (QOL) of the patients.

The invention claimed is:

1. A method for producing gelatin particles, comprising:
    discharging droplets of a liquid containing melted gelatin into an atmosphere in a heating tube or a drying chamber, wherein a first temperature of the atmosphere is higher than a second temperature of the liquid, and a difference between the first temperature and the second temperature is 235° C. or less; and
    drying the droplets in the atmosphere to obtain gelatin particles,
    wherein a weight-average molecular weight of a gelatin of the gelatin particles is in a range of 1000 or more to 100000 or less, and
    when a major-axis length of the gelatin particles is defined as a and a major-axis length of the gelatin particles obtained in a case where a swelling treatment is carried out by immersing the gelatin particles into water at 40° C. under an atmospheric pressure for 60 minutes is defined as b, a swelling degree represented by b/a is 1.0 to 10.0, and wherein a particle diameter of the gelatin particles obtained in the case where the swelling treatment is carried out is 1.0 nm to 5.0 μm.

2. The method for producing gelatin particles according to claim 1, wherein the droplets are discharged from a nozzle of an inkjet head.

3. The method for producing gelatin particles according to claim 1, wherein the gelatin particles have an aspect ratio in a range of 1.0 to 1.4.

4. The method for producing gelatin particles according to claim 1, wherein the major-axis length b of the gelatin particles obtained in the case where the swelling treatment is carried out is 2.0 μm or less.

5. The method for producing gelatin particles according to claim 1, wherein the gelatin particles further comprise a contrast medium.

6. The method for producing gelatin particles according to claim 1, wherein the gelatin of the gelatin particles is crosslinked.

7. The method for producing gelatin particles according to claim 1, wherein the gelatin of the gelatin particles is crosslinked by self-crosslinking.

8. The method for producing gelatin particles according to claim 1, wherein the gelatin of the gelatin particles is crosslinked by self-crosslinking by heat or UV irradiation.

9. The method for producing gelatin particles according to claim 1, wherein the difference between the first temperature and the second temperature is in a range of 20 to 235° C.

10. The method for producing gelatin particles according to claim 1, wherein a gelatin content of the liquid containing the melted gelatin is in a range of $1.00 \times 10^{-8}$ vol % or more to 60 vol % or less.

11. The method for producing gelatin particles according to claim 1, wherein the first temperature is in a range of 40° C. or higher to 250° C. or lower, and the second temperature is in a range of 15° C. or higher to 80° C. or lower.

* * * * *